Dec. 10, 1946. W. E. LAMMERTS Plant Pat. 716
ROSE PLANT
Filed Jan. 17, 1946
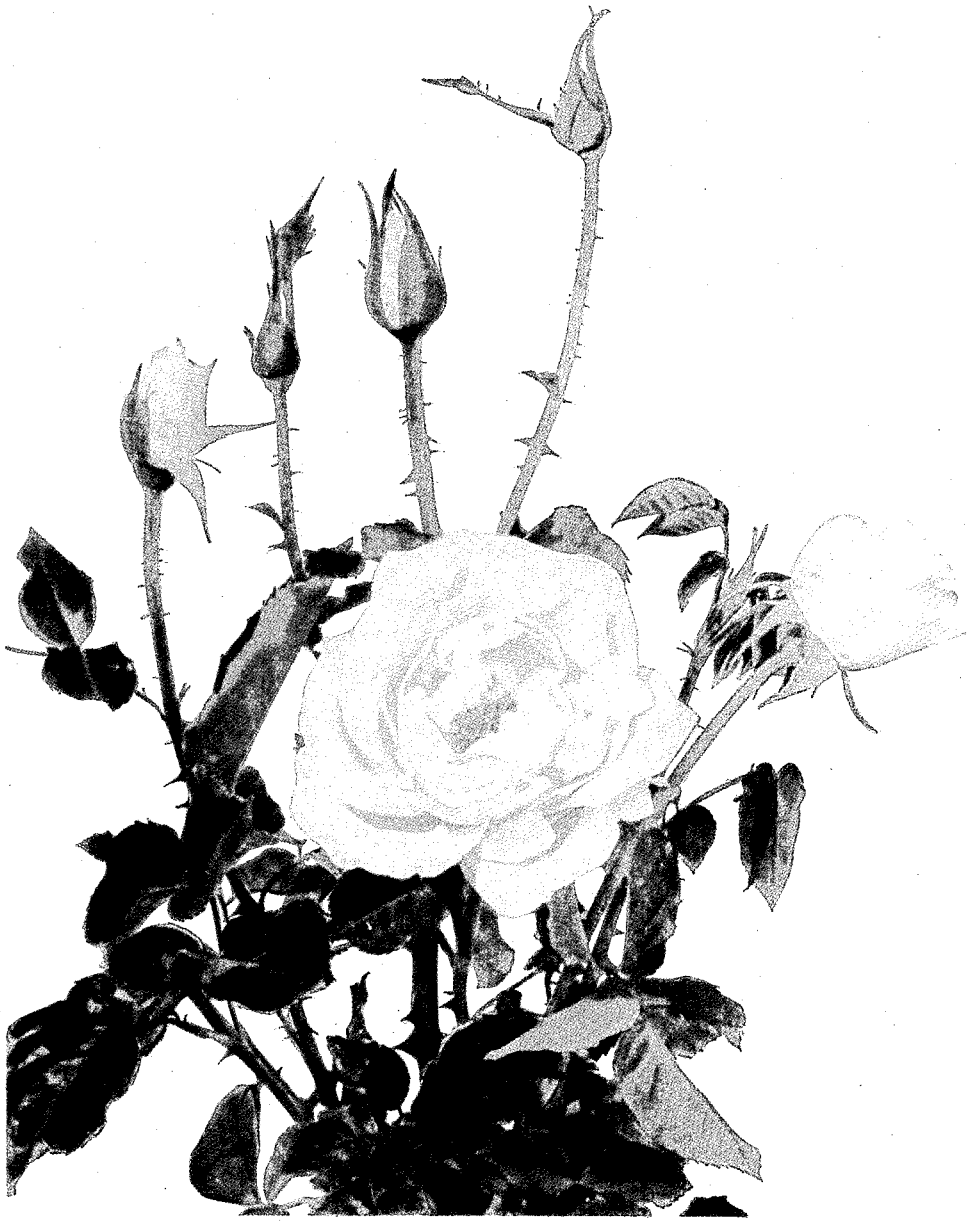
Inventor
W. E. Lammerts
By Robbins & Robbins
Attorneys Patented Dec. 10, 1946

Plant Pat. 716

UNITED STATES PATENT OFFICE

716

ROSE PLANT

Walter E. Lammerts, La Canada, Calif., assignor to Armstrong Nurseries, Inc., Ontario, Calif., a corporation of California Application January 17, 1946, Serial No. 641,666

1 Claim. (Cl. 47—61)

The present invention relates to a new and distinct variety of hybrid tea rose plant, resulting from a definite effort to produce a rose which would combine the best characteristics of two well-known varieties, "Mrs. Sam McGredy" and "President Herbert Hoover," while eliminating some of the undesirable characteristics of the individual parents.

In order to best appreciate the distinguishing features of this new rose, a comparison of the same with each of the parents will now be made.

The variety "Mrs. Sam McGredy," the seed parent, has a strong and pleasing flower color in salmon-orange and pink shades. These flowers are borne on a plant with handsome, glossy foliage which is weak and spreading and has also a tendency to produce willowy-growth.

The variety "President Herbert Hoover" is characterized by extremely vigorous, upright growth, with long, strong stems, but with foliage dull in appearance and quite susceptible to mildew. Its flowers are not strongly colored and are often characterized by the presence of an objectionable blue pigment in the outer extremities of the flower and with a pale, quick-fading center.

This new variety is a combination of the dominant characteristics of both parents, that is, the strongly colored flower of the seed parent and the habit and vigor of growth of the pollen parent. In other respects, the petals of the new rose have more substance, and the flowers more fragrance, said flowers being borne on stronger and longer stems than those of "Mrs. Sam McGredy." The foliage is glossy and resistant to mildew. This foliage on new growth has a predominating shade of red, as hereinafter set forth specifically, more nearly typical of "Mrs. Sam McGredy," but slightly darker, and both new and mature foliage are heavier and larger than that of either parent.

Further, this new rose has a greater freedom of bloom than either of its parents, as well as a more attractive shape in the bud. The length of bud is comparable to that of the pollen parent, but the form is more graceful because of the typical urn-shape as compared with the somewhat stiff pointed bud of said parent. The bud, furthermore, is longer than that of the seed parent and more gracefully shaped because of its urn-shape characteristic. It is further characterized by fluted or ruffled edges of the petals which are quite pronounced in the bud.

Perhaps the most predominant characteristic of this new rose is found in the novel color combination of its flowers running from chrome yellow at the base, gradually shading into other colors progressing towards the outer circumference through shades of rose, pink, madder, carmine, begonia and others as shown in the accompanying drawing as nearly as possible to depict in detail.

Because of the combination of all these characteristics in this new variety, it is easily and importantly distinguishable from any other variety now known in commerce.

In the accompanying drawing are shown specimens of the new variety in the different stages of development of the flower from bud to fully-open bloom, together with new and mature foliage.

Asexual reproduction shows that the characteristics hold true through succeeding propagations.

The following is a detailed description of the new variety, all reference to color being in accordance with the R. F. Wilson's Horticultural Colour Chart, except where indicated to be in accordance with Ridgway's Color Standard and Nomenclature:

Class: Hybrid tea.
Type: Tall; bush; outdoor; seedling; for cut flowers and garden decoration.
Breeding: Seedling.
*Seed parent.*—"Mrs. Sam McGredy."
*Pollen parent.*—"President Herbert Hoover."
Propagation: By budding, the only method tried so far.

*Flower*

Locality where grown: Ontario, California.
Flowers borne: Singly to three and four to stem; in irregular cluster; on normally strong, medium-long stems.
Quantity of bloom: Free; outdoors.
Continuity: Continuous during growing season.
Fragrance: Moderate; spicy.
Bud:
*Peduncle.*—Medium long; heavy; erect; rough; numerous gland-tipped cilia and prickles; near Parrot Green, Plate VI (Ridgway), to Ocher Red, Plate XXVII (Ridgway), on side exposed to sun.
*Before calyx breaks.* — *Size* — medium. *Form*—Medium long; pointed; with foliaceous appendages, glabrous otherwise, on the surface of the bud; with medium-stout much-cut foliaceous parts extending beyond the tip of the bud equal to one-half or more of its length.

*As calyx breaks.*—*Color*—near Straw Yellow, Plate 604, page 67, at base, gradually becoming washed with Claret Rose, Plate 021, page 109, to Rose Red, Plate 724, page 158, progressing toward apex. *Calyx inner surface*—with fine, woolly tomentum. Margins lined with stipitate glands and hairs unless adjacent sepals cover margin, then only woolly tomentum is found on margin covered.

*As first petal opens.*—*Size*—medium. *Form*—medium long; urn. *Color*—outside: near Chinese Yellow, Plate 606, page 68, at base, gradually changing to Carmine, Plate 21/1, page 21, beginning about one-third way from base to apex and continuing on to apex, but blotched with near Claret Rose, Plate 021, page 109; inside: Chinese Yellow, Plate 606, page 68, at base, gradually changing to Carmine Rose, Plate 621, page 75, beginning about one-third way from base to apex and continuing on to apex, but slightly shaded by Phlox Pink, Plate 625/1, page 77, near apex.

*Opening.*—Opens up well. Is not retarded from opening by cold, hot, wet or dry weather.

Bloom:

*Size.*—When fully open—medium; 3¼ inches to 3¾ inches.

*Petalage.*—Semi-double to double (but the stamens not hidden); from 16 to 22 petals, plus 3 to 5 petaloids.

*Form.*—Cupped; petals at first cupped with tips rolled outward; becoming later, at maturity, loosely flat-cupped with tips rolled outward.

Petals: medium thick; with inside slightly velvety and outside satiny.

*Shape.*—Outside — broadly obovate-cuneate with apex flat. Intermediate—obovate-cuneate, with apex flat. Inside—narrowly obovate-cuneate, with apex flat.

*Color.*—Colors may be modified by being bordered, blotched and/or washed with other colors.

This description of a newly opened flower was made from a rose grown outdoors in the month of October, 1945, at Ontario, California:

*Color.*—*Outside petal*—outside surface: near Chrome Yellow, Plate 605, page 144, gradually changing to Carmine, Plate 21/1, page 21, beginning about one-third of the way from base toward apex and continuing to apex but blotched with Rose Madder, Plate 23/1, page 23; inside surface: Chrome Yellow, Plate 605, page 144, at base, gradually becoming Neyron Rose, Plate 623, page 76, to Delft Rose, Plate 020/1, page 108, washed with Phlox Pink, Plate 625/2, page 77, near apex. *Intermediate petal*—outside surface: Chrome Yellow, Plate 605, page 144, at base, gradually becoming Carmine Rose, Plate 621/1, page 75, at border on upper one-half of petal; inside surface: Chrome Yellow, Plate 605, page 144, at base, gradually becoming Carmine Rose, Plate 621 page 75, to Begonia, Plate 619/1, page 146, slightly shaded with Phlox Pink, Plate 625/2, page 77, near apex. *Inner petal*—outside surface: Chrome Yellow, Plate 605, page 144, at base, gradually becoming Carmine Rose, Plate 621/1, page 75, at border on upper one-half of petal; inside surface: Chrome Yellow, Plate 605, page 144, at base, gradually becoming Carmine Rose, Plate 621, page 75, to Begonia, Plate 619/1, page 146, slightly washed with Phlox Pink, Plate 625/2, page 77, at apex.

This description was made from a rose that was open for three days outdoors in the month of October, 1945, at Ontario, California:

*Color.*—*Outside petal*—outside surface: near Straw Yellow, Plate 604, page 67, at base, gradually changing to Porcelain Rose, Plate 620/2, page 147, beginning about one-third of way from base toward apex and continuing to apex; inside surface: near Chrome Yellow, Plate 605, page 144, at base, gradually changing to Neyron Rose, Plate 623/1, page 76, but washed with Phlox Pink, Plate 625/1, page 77, beginning one-quarter of way from base toward apex and continuing to apex. *Inside petal*—outside surface: Straw Yellow, Plate 604/1, page 67, at base, gradually becoming Porcelain Rose, Plate 620/3, page 147, at border beginning one-third of way from base toward apex and continuing to apex; inside surface: Chrome Yellow, Plate 605, page 144, at base, gradually changing to Neyron Rose, Plate 623/1, page 76, but washed with Phlox Pink, Plate 625/2, page 77, beginning one-quarter of way from base toward apex and continuing to apex.

*General color effect.*—Newly opened flower—near Carmine Rose, Plate 621, page 75, to Begonia, Plate 619/1, page 146. Three days open—near Neyron Rose, Plate 623/1, page 76, washed with Phlox Pink, Plate 625/2, page 77, at apex.

*Behavior.*—Drop off cleanly; fading to near Neyron Rose, Plate 623/2, page 76, with Phlox Pink, Plate 625/2, page 77, shading. Fading lighter in hot weather.

*Flower longevity.*—On bush in garden—three days in October. Cut roses grown outdoors, kept at living room temperatures—two to three days in October.

*Reproductive organs*

Stamens: Many; arranged regularly about pistils, mixed with petaloids.

Filaments: Medium to long; 4 to 10 mm. in length.

*Color.*—Near Nasturtium Orange, Plate 610/1, page 145. Most with anthers.

Anthers: Medium size; all open at once approximately.

*Color.*—Near Straw Yellow, Plate 604/2, page 67, bordered with Maize Yellow, Plate 607/1, page 69.

Pollen: Sparse; near Yellow Ochre, Plate 07, page 101.

Pistils: Many, near sixty in number.

Styles: Very even; medium long; medium heavy; loosely bunched.

*Color.*—Blood Red, Plate 820/3, page 166, to near Chartreuse Green, Plate 663/1, page 90, at base.

Stigma: Grayish white, somewhat translucent.

Ovaries: Some protruding from calyx.

Hips: Globular, somewhat flattened at top.

*Color.*—On side exposed to sun, near Aniline Yellow, Plate IV (Ridgway). On side not exposed to sun, near Pyrite Yellow, Plate IV (Ridgway). Moderately smooth; walls thick; fleshy.

Sepals: Permanent until hip matures, then deciduous; medium long; recurved.

*Color.*—Inside, from fully open flower—Deep Sea-foam Green, Plate XXXI (Ridgway), in center of base bordered by Deep Chrysolite Green, Plate XXXI (Ridgway). Outside, from fully open flower—Light Cress Green, Plate XXXI (Ridgway), to Chrysolite Green, Plate XXXI (Ridgway), at base.

Seeds: Few, six to ten in number; large.

*Plant*

Foliage:

*Leaves.*—Compound of three to five leaflets; normally abundant; medium to large; heavy; glossy.

*Leaflets.*— Shape — oblong-lanceolate with apex acute; base round; margin doubly serrate.

*Color.*—*Mature*—upper surface: near Parsley Green, Plate 00962, page 193: under surface: near Lavender Green, Plate 00761, page 196. *Young*—upper surface: near Victoria Lake, Plate I (Ridgway); under surface: Vandyke Red, Plate XIII (Ridgway).

*Rachis.*—Medium heavy; upper side, grooved, glandular. Under side, moderately prickly, and with stipitate glands.

*Stipules.*—Medium length; medium wide; short to medium points, turning out at an angle of more than 45°, recurved toward the stem.

*Disease.*—Moderately resistant to mildew.

Growth:

*Habit.*—Upright; much branched.

*Growth.*—Free.

*Canes.*—Medium heavy.

*Main stems.*—Rainette Green, Plate XXXI (Ridgway). *Large prickles*—several; medium length; slightly hooked downward; with medium narrow base. Color—near Rood's Brown, Plate XXVIII (Ridgway). *Small prickles*—few. Color—near Rood's Brown, Plate XXVIII (Ridgway). *Hairs*—none.

*Branches.*—Light Cress Green, Plate XXXI (Ridgway). *Large prickles*—several to many; medium length; slightly hooked downward; with medium narrow base. Color—near Rose Pink, Plate XII (Ridgway) becoming Pale Turtle Green, Plate XXXII (Ridgway) at point. *Small prickles* — several. Color — near Rose Pink, Plate XII (Ridgway) at base, becoming Pale Turtle Green, Plate XXXII (Ridgway) at point. *Hairs*—none.

*New shoots.*—Near Absinthe Green, Plate XXXI (Ridgway) gradually becoming washed with Erythrite Red, Plate 0027, page 190. *Large prickles*—several; medium, slightly hooked downward, with medium narrow base. Color—Rhodonite Red, Plate 0022, page 188. *Small prickles*—several. Color—Rhodonite Red, Plate 0022, page 188. *Hairs*—none.

I claim:

A new and distinct variety of Rose plant, characterized as to novelty by its habit and vigor of growth; glossy foliage resistant to mildew; the red color of the new growth foliage; the heavier and large size of both new and mature foliage as compared with that of either parent; freedom of bloom; shape and form of bud; and the fragrance and unusual coloring of the flowers, substantially as shown and described.

WALTER E. LAMMERTS.